United States Patent
Kaiser et al.

[11] Patent Number: 5,501,344
[45] Date of Patent: Mar. 26, 1996

[54] PROCESS FOR THE IDENTIFICATION OF RANDOMLY SHAPED AND/OR PLANE MATERIALS BY DETERMINATION OF THE STRUCTURE OF THE MATERIALS THROUGH APPLICATION OF ELECTROMAGNETIC AND/OR ACOUSTIC WAVES

[75] Inventors: Dieter Kaiser, Dortmund; Franz Wintrich, Essen, both of Germany

[73] Assignee: RWE Entsorgung, Germany

[21] Appl. No.: 422,761

[22] Filed: Apr. 14, 1995

Related U.S. Application Data

[63] Continuation of Ser. No. 139,925, Oct. 20, 1993, abandoned.

[30] Foreign Application Priority Data

Oct. 23, 1992 [DE] Germany ............... 42 35 956.2

[51] Int. Cl.⁶ ..................................... B07C 5/00
[52] U.S. Cl. ................... 209/578; 209/587; 209/930
[58] Field of Search ............................ 209/577, 578, 209/587, 598, 930, 939

[56] References Cited

U.S. PATENT DOCUMENTS

| | | | |
|---|---|---|---|
| 4,600,105 | 7/1986 | Van Zyl et al. | 209/587 |
| 4,915,827 | 4/1990 | Rosenthal | 209/577 |
| 5,134,291 | 7/1992 | Ruhl, Jr. et al. | 209/587 X |
| 5,141,111 | 8/1992 | Licht | 209/577 X |
| 5,158,181 | 10/1992 | Bailey | 209/587 X |
| 5,190,163 | 3/1993 | Anzai et al. | 209/577 X |
| 5,206,699 | 4/1993 | Stewart et al. | 209/577 X |
| 5,260,576 | 11/1993 | Sommer, Jr. et al. | 209/577 X |
| 5,273,166 | 12/1993 | Sawamura | 209/587 |

*Primary Examiner*—D. Glenn Dayoan
*Attorney, Agent, or Firm*—Connolly & Hutz

[57] ABSTRACT

Acoustic or electromagnetic wave energy (UV-, visible or infrared, preferably electromagnetic, particularly UV- or visible) is applied to randomly-shaped or plane materials or mixtures of such materials, whereby the materials are irradiated and the structures of the materials, particularly the surface structures of the materials, are determined by identification of the waves which arrive from the irradiated materials at a receiver-sensor, equipped with a data logger, and comparison of the thus-received data with the data of the data logger. A sorting device for sorting out thus-identified materials is operated with the aid of signals arriving from the receiver-sensor.

12 Claims, No Drawings

PROCESS FOR THE IDENTIFICATION OF RANDOMLY SHAPED AND/OR PLANE MATERIALS BY DETERMINATION OF THE STRUCTURE OF THE MATERIALS THROUGH APPLICATION OF ELECTROMAGNETIC AND/OR ACOUSTIC WAVES

CROSS-REFERENCE TO RELATED APPLICATION

This application is a continuation of application Ser. No. 139,925, filed Oct. 20, 1993 now abandoned.

FIELD OF THE INVENTION

The instant invention relates to the application of electromagnetic waves in the UV-, visible and infrared range and/or of acoustic waves for the identification of randomly shaped and/or plane materials. According to this invention, the materials are irradiated and the structures of the materials are determined, in particular the surface structures of the materials, by identification of the waves, which arrive from the irradiated materials at a receiver-sensor, equipped with a reference data logger, and comparison of the received data with data of the data logger and whereby a sorting device for sorting out identified materials is operated with the aid of signals arriving from the receiver-sensor.

DESCRIPTION OF THE PRIOR ART

Separating and sorting are important processes in industry, trade and household.

To date, these processes are still carried out essentially by manual labor, although modern, fully automatic separating units are known, which are capable of identifying objects on the basis of characteristics, like size, shape, colour, printing, specific marks, like trade marks etc. and which put in operation sorting devices for sorting out identified objects. A well-known example is sorting out of products of inferior quality in the food industry, for example in the case of packaging of coffee-beans and other food and luxury food.

Developments of this kind are also known in the field of recycling valuable components from waste.

Thus DE-OS 4018 757 discloses sorting of materials by taking advantage of different heat-absorption of electrically conductive and non-conductive waste materials.

To this, individualized objects on a conveyer belt are irradiated with infrared radiation, distinct emissions of heat are recorded and by signals from the receiver-sensor a sorting device is put in operation.

In DE-OS 4021 882 a process for the identification of individual plastic materials is described. In this process a mixture of different plastics, for example from waste, is irradiated by microwaves, whereby again the individual emission of heat is used for putting in operation a sorting device. For measuring the heat emission, preferably a pyrometer is used.

DE-OS 4212 713 discloses a system for recycling containers, which is equipped with a receiver-sensor, which identifies and evaluates among others also surfaces.

On page 2 of the specification it is outlined that the characteristic patterns. which are identified, like diamond-shaped design, nap-design or grooves on the surface of the containers are such patterns, which have been incorporated already by the producer into the container surfaces.

In DE-OS 4125 045 a process for sorting of waste mixtures is disclosed, which is characterized by irradiation of the individual waste objects with electromagnetic and/or acoustic waves, recording of the waves arriving from the irradiated objects by a receiver-sensor for identification of the objects and by passing signals from the receiver-sensor to a sorting device, which sorts out the identified waste objects.

The receiver-sensor records informations, like the shape of the object, for example bottle-, beaker-, cup- or tube-shapes and other shapes, as well as printing, product-names, company- and producer-names, trade-marks or colours.

Hitherto the problem has not been solved, which consists of sorting objects, which possess random and/or plane shapes, and which are not characterized by specific colours, printing etc., for example paper, cardboard, foils or textiles, which may be either unused or waste, furthermore rubble, which may consists of numerous materials, shredder waste, for example from car-shredding and other materials.

SUMMARY OF THE INVENTION

Applicant has found a non-obvious solution to this problem by a process, which uses electromagnetic waves in the UV-, visible or infrared range and/or acoustic waves for the identification of randomly shaped and/or plane materials, characterized in that the materials are irradiated, the waves are identified, which arrive from the irradiated materials, the structures are recorded, in particular the surface fine-structures of the materials by a receiver-sensor device, equipped with a data logger whereby the data received are compared to data stored in the data logger and whereby the data stored, embrace a sufficient number of surface-characteristics of randomly shaped materials and in that a sorting device for sorting out identified materials is controlled by signals from the receiver-sensor.

DETAILED DESCRIPTION

It is generally known that plane materials possess a surface fine-structure, independent of specific patterns, like diamond-shaped, nap-shaped designs, grooves or other patterns, which have been incorporated already by the producer. Thus cardboard has a surface fine-structure, which is different to the surface fine-structure of glazing paper or typewriter paper. Again a coated paper possesses still another surface fine-structure.

Paper in general has a surface fine-structure different to plastic foils. Plastic foils among themselves also exhibit different and characteristic surface fine-structures, which often depend on the type of production unit, but may also depend on the chemical structure of the foil.

The instant invention is very well suited for the identification of plane materials like paper, cardboard, foils, textiles and others, independent of the quality of the materials i.e. whether they are new or used, respectively waste materials.

A regular outer shape or size of the materials to be identified is of no or only little importance, since a sufficient number of data of randomly shaped materials is available in the data logger for comparison with data obtained from the irrediated objects. Thus the materials may be scrap with random irregular edges. In general also the thickness of the materials is unimportant.

Depending on the resolving power of the electromagnetic waves used for the irradiation of the materials, the surface fine-structure is additionally recorded and compared to data stored in the data logger. In this way the identification of specific surfaces and consequently specific materials is possible according to the invention, whereby the identification of the surface fine-structure is often sufficient for identification. By specific signals directed to a sorting device, which may be operated pneumatically or mechanically or by other technics, sorting out of the identified materials can be carried out.

According to the invention, rubble can be sorted with very good results, since, based on the structure of the material, in particular of the surface structure, materials like wood, light weight construction materials, brick material, ceramic material, metals, glass and others can be separated very reliably, even if these materials don't possess a definite shape, but are randomly crushed or broken.

The structure of the site of fracture may be of importance according to the instant invention.

As a supporting means, for the identification of surface fine-structures of objects, images of the objects obtained by recording the waves, which arrive from the irradiated objects, may be enlarged. As a result, the enlarged characteristic structures can be identified by comparison with structure-data, stored in the data logger.

Other marks on the surface of objects, if present, like printings of names, trade marks, colours etc. can be additionally used for identification.

UV- and visible light is preferred according to the invention.

Acoustic waves can be used according to the invention, if the resolving power is sufficient.

Use of infrared radiation may be useful, if, as a consequence of different surface structures, a different temperature increase occurs, whereby the emission of heat is also recorded by the recorder-sensor.

It is of major importance that the materials to be sorted out, are sufficiently individualized respectively separated on the conveyer belt from each other.

Receiver-sensors are known to persons skilled in the art. They may be equipped with cameras, video cameras, magnifying devices, sound-sensitive devices and other suitable devices.

Radiating devices and sources which emit electromagnetic or acoustic waves are also known to persons skilled in the art, as well as separating and sorting devices, which may be operated pneumatically, mechanically, hydraulically, electrostatically or in other ways.

We claim:

1. A process for identifying and sorting randomly-shaped or plane material or mixtures thereof, comprising:

irradiating the surface structure of randomly-shaped or plane or mixed randomly-shaped/plane material with electromagnetic waves in the UV- or visible portion of the electromagnetic spectrum, resulting in image producing waves emitted from said surface structure, recording the image producing waves arriving from the thus-irradiated material in a receiver-sensor device equipped with a data logger, said data logger having stored therein data relating to a sufficient number of surface characteristics of randomly-shaped or plane material to identify such material, comparing the image recorded in accordance with surface fine-structure in said material, from the waves arriving from the thus-irradiated material to said data stored in said data logger to identify the thus-irradiated material, and generating a signal, with said receiver-sensor, for controlling a sorting device, and sorting said thus-irradiated material by means of a sorting device controlled by a said signal received from said receiver-sensor device.

2. Process according to claim 1, wherein the thus-irradiated material is a waste mixture containing plane material, and wherein said sorting step sorts out the plane material from the waste mixture.

3. Process according to claim 2, wherein said plane material comprises paper, cardboard, foil, textile material, or a mixture thereof.

4. Process according to claim 1, wherein the thus-irradiated material is a mixture containing rubble components, and wherein said sorting step sorts out the rubble from said mixture.

5. Process according to claim 1, wherein identification in accordance with the surface fine-structure of said material is improved by recording the waves arriving from the thus-irradiated material as an image of said material, magnifying this recorded imager and comparing said image to said data stored in said data logger.

6. Process according to claim 1, wherein the thus-irradiated material is also identified by identifying surface characteristics incorporated into the surface of said material by the producer of the material.

7. Process according to claim 6, wherein said surface characteristics are printings, marks, colors, incorporated structures, or a combination thereof.

8. A process for identifying and sorting randomly-shaped or plane material or mixtures thereof, comprising:

irradiating the surface structure of randomly-shaped or plane or mixed randomly-shaped/plane material with electromagnetic waves in the UV- or visible portion of the electromagnetic spectrum, resulting in image producing waves emitted from said surface structure, recording the image producing waves arriving from the thus-irradiated material in a receiver-sensor device equipped with a data logger, said data logger having stored therein data relating to a sufficient number of surface characteristics of randomly-shaped or plane material to identify such material, comparing the image recorded from the waves arriving from the thus-irradiated material to said data stored in said data logger to identify the thus-irradiated material, the thus irradiated material is identified by identifying surface characteristics incorporated into the surface of said material by the producer of said material and generating a signal, with said receiver-sensor, for controlling a sorting device, and sorting said thus-irradiated material by means of a sorting device controlled by a said signal received from said receiver-sensor device.

9. The process according to claim 8, wherein said surface characteristics are printings, marks, colors, incorporated structures, or a combination thereof.

10. The process according to claim 8, wherein the thus-irradiated material is a waste mixture containing plane material, and wherein said sorting step sorts out the plane material from the waste mixture.

11. Process according to claim 8, wherein said plane material comprises paper, cardboard, foil, textile material, or a mixture thereof.

12. Process according to claim 8, wherein the thus-irradiated material is a mixture containing rubble components, and wherein said sorting step sorts out the rubble from said mixture.

* * * * *